United States Patent
Benderson et al.

(10) Patent No.: US 10,155,112 B2
(45) Date of Patent: Dec. 18, 2018

(54) APPARATUS FOR NEUROSTIMULATION

(71) Applicant: Meredith Benderson Hillig, Bethesda, MD (US)

(72) Inventors: Meredith Benderson, Bethesda, MD (US); Brian Jamieson, Severna Park, MD (US)

(73) Assignee: Meredith Benderson Hillig, Bethesda, MD (US)

( * ) Notice: Subject to any disclaimer, the term of this patent is extended or adjusted under 35 U.S.C. 154(b) by 242 days.

(21) Appl. No.: 14/696,361

(22) Filed: Apr. 24, 2015

(65) Prior Publication Data

US 2015/0306386 A1 Oct. 29, 2015

Related U.S. Application Data

(60) Provisional application No. 61/984,065, filed on Apr. 25, 2014.

(51) Int. Cl.
| | | |
|---|---|---|
| *A61N 1/36* | (2006.01) | |
| *A61N 2/02* | (2006.01) | |
| *A61H 39/00* | (2006.01) | |
| *A61H 39/08* | (2006.01) | |

(52) U.S. Cl.
CPC ....... *A61N 1/36017* (2013.01); *A61H 39/002* (2013.01); *A61H 39/08* (2013.01); *A61N 2/02* (2013.01); *A61H 2039/005* (2013.01); *A61H 2201/165* (2013.01); *A61H 2201/501* (2013.01); *A61H 2201/5002* (2013.01); *A61H 2201/5097* (2013.01)

(58) Field of Classification Search
CPC ..... A61B 5/042; A61B 5/0464; A61B 5/4836; A61N 1/0504; A61N 1/0563; A61N 1/3621; A61N 1/3622; A61N 1/3931; A61N 1/3962
See application file for complete search history.

(56) References Cited

U.S. PATENT DOCUMENTS

| | | | |
|---|---|---|---|
| 3,908,699 A | 9/1975 | Umphenour et al. | |
| 4,398,545 A | 8/1983 | Wilson | |
| 5,950,635 A | 9/1999 | Garcia-Rill et al. | |
| 6,961,622 B2 | 11/2005 | Gilbert | |
| 7,120,499 B2 * | 10/2006 | Thrope | A61N 1/0551 607/115 |
| 7,571,002 B2 | 8/2009 | Thrope et al. | |
| 8,024,045 B2 * | 9/2011 | Carlton | A61B 5/6864 600/378 |
| 8,086,318 B2 | 12/2011 | Strother et al. | |

OTHER PUBLICATIONS http://www.homedics.com/rapid-relief-electronic-pain-relief-pad-for-arms-legs.html (printed Aug. 26, 2015).
http://omronpainrelief.com (printed Aug. 26, 2015).

(Continued)

*Primary Examiner* — Amanda Hulbert
(74) *Attorney, Agent, or Firm* — Cermak Nakajima & McGowan LLP; Adam J. Cermak (57) ABSTRACT

Various systems and methods related to the design and manufacturing of wearable patches for long-term, controlled stimulation of highly-localized regions on the skin of a wearer, including for the practice of acupuncture, are disclosed and claimed.

20 Claims, 7 Drawing Sheets

(56) References Cited

OTHER PUBLICATIONS http://www.lgmedsupply.com/tenz500.html?gclid=CNXFw4nfpbwCFY9IOgodMT4ATw (printed Aug. 26, 2015).
http://www.lhasaoms.com/Ear-Pellets-and-Acu-Magnets.html (printed Aug. 26, 2015).
http://www.alibaba.com/product-gs/1610284508/acupuncture_pain_relief_patch_by_CE.html (printed Aug. 26, 2015).
http://www.gizmag.com/wireless-acupuncture-patch/23586/ (printed Aug. 26, 2015).
http://www.fastcoexist.com/1680166/a-new-high-tech-upgrade-to-acupuncture-lets-you-see-its-working-in-real-time (printed Aug. 26, 2015).

* cited by examiner

APPARATUS FOR NEUROSTIMULATION

REFERENCE TO EARLIER APPLICATION

This Application incorporates by reference and, under 35 U.S.C. § 119(e), claims priority to U.S. Provisional Patent Application Ser. No. 61/984,065 filed on Apr. 25, 2014.

STATEMENT REGARDING FEDERALLY SPONSORED RESEARCH OR DEVELOPMENT

This invention is not the subject of federally sponsored research or development.

RESERVATION OF COPYRIGHTS

Portions of the disclosure of this document contain material that is subject to copyright protection. The copyright owner has no objection to any reproduction of the document or disclosure as it appears in official records, but reserves all remaining rights under copyright.

BACKGROUND OF THE INVENTION

The practice of acupuncture relies upon the application of a mechanical and/or electrical stimulus at a highly localized region of a patient's skin. Acupuncture is carried out by trained practitioners who direct stimuli to specific areas, and it is generally practiced in an acute manner, meaning that therapy is applied by the practitioner for the duration of a session, after which it is terminated.

It has been postulated that the ability to deliver acupuncture chronically and continuously, that is for periods of hours, days or weeks, could improve the outcomes for the practice of acupuncture.

Current methods, which employ needles placed by a practitioner to stimulate acupuncture points, and through which (optionally) an electrical current is applied, are not practical for long term use since the needles interfere with normal clothing and pose a hazard for injury if left in place outside of the acupuncture session. In addition, current methods for stimulating acupuncture points do not allow for periodic, intermittent or otherwise controlled stimuli over long durations. An acupuncture needle introduced in the skin, for example, continuously stimulates a response for as long as it is in place. Electrical stimulation, when applied, must be controlled by some device connected to the recipient, which necessitates a wired connection between recipient and some external electronics, as well as intervention from an operator or practitioner if stimulation conditions (i.e. current on/off, or current intensity) are to be varied.

Acupuncture applied in a controlled and chronic basis may have applications to treating a wide variety of disorders including depression and anxiety, musculoskeletal pain, drug and alcohol addiction, menstrual cramping, and other causes of pain. In addition such a system may be useful for inducing or terminating a pregnancy.

There is a need for systems and methods that address shortcomings in the art. Specifically, it is desirable to provide stimuli to one or more acupuncture points for long periods of time, spanning hours or days. During such long-term treatment, it would be desirable to control or manipulate the duty cycle, intensity, waveform, frequency, and other stimulation parameters automatically during the application of the stimuli. Accordingly, a device for providing such therapy should be small (i.e. thin and occupy a small area), fully autonomous (i.e. not connected or wired to other units or components) and capable of operating autonomously for days or weeks without any operator intervention. The device should also contain a practical, compact and integrated device for providing highly localized stimulation to the acupuncture point.

The invention provides improved elements and arrangements thereof, for the purposes described, which are inexpensive, dependable and effective in accomplishing intended purposes of the invention.

Other features and advantages of the invention will become apparent from the following description of the preferred embodiments, which refers to the accompanying drawings.

BRIEF DESCRIPTION OF THE DRAWINGS

The invention is described in detail below with reference to the following figures, throughout which similar reference characters denote corresponding features consistently, wherein.

DETAILED DESCRIPTION OF THE PREFERRED EMBODIMENTS

This disclosure is not limited in application to the details of construction and the arrangement of components set forth or illustrated in the drawings herein. The disclosure is capable of other embodiments and of being practiced or of being carried out in various ways. Phraseology and terminology used herein is for description and should not be regarded as limiting. Uses of "including," "comprising" or "having" and variations thereof herein are meant to encompass the items listed thereafter and equivalents thereof as well as additional items. Unless limited otherwise, "connected," "coupled" and "mounted," and variations thereof herein are used broadly and encompass direct and indirect connections, couplings, and mountings. "Connected" and "coupled" and variations thereof are not restricted to physical or mechanical or electrical connections or couplings. Furthermore, and as described in subsequent paragraphs, the specific mechanical or electrical configurations described or illustrated are intended to exemplify embodiments of the disclosure. However, alternative mechanical or electrical configurations are possible, which are considered to be within the teachings of the disclosure. Furthermore, unless otherwise indicated, "or" is to be considered inclusive.

The invention provides stimuli to one or more acupuncture points for long periods of time, spanning hours or days. During long-term treatment, the invention controls or manipulates the duty cycle, intensity, waveform, frequency, and other stimulation parameters automatically during the application of the stimuli. The invention provides a device for providing such therapy that is small (i.e. thin and occupy a small area), fully autonomous (i.e. not connected or wired to other units or components) and capable of operating autonomously for days or weeks without any operator intervention. The invention provides a practical, compact and integrated device for providing highly localized stimulation to an acupuncture point.

Figure 1:
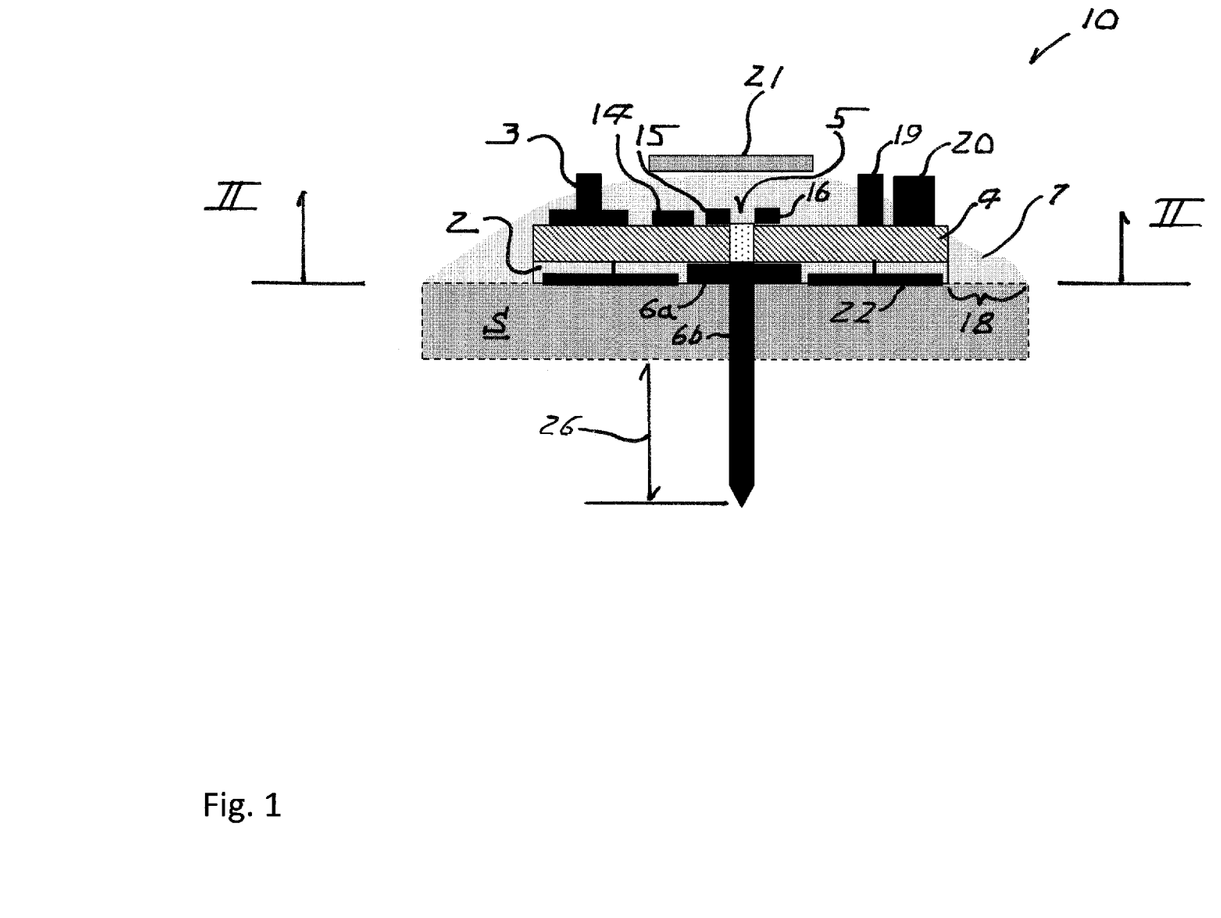
FIG. 1 is a cross-sectional detail view of embodiments of an apparatus for neurostimulation configured according to principles of the invention.

Referring to FIG. 1, an embodiment of an apparatus 10 for neurostimulation configured according to principles of the invention includes at least an electrode 6 mounted on an electrical connector 5. Electrical connector 5 is connected to a circuit board 4 on which various electrical components are mounted. A backing 2 mounts on circuit board 4 and can be adhered to a skin S. A cover 7 adhesively mounts on patient's skin S and potentially, but not necessarily on backing 2, circuit board 4, the electrical components or electrical connector 5.

Circuit board 4 essentially provides a communications circuit (not shown) with which controller 14 and the various electrical components mounted thereon communicate, and an energy circuit (not shown) for delivering electrical or electrically-induced stimulus to electrode 6.

Electrode 6 has a needle 6b with an anchor 6a. Needle 6b has a length 26 extending from anchor 6a that ranges from 0.5 mm to 25 mm or otherwise appropriately configured to provide sufficient penetration depth to pass the epidermis without posing a health hazard to the patient.

Electrode 6 is constructed, arranged and configured to be insulated from circuit board 4, or at least the communications circuit (not shown) thereof, and have needle 6b operatively connected or in communication with the energy circuit (not shown). To this end, anchor 6a may be constructed of non-conductive material. Needle 6b is constructed of metal or other material, such as a polymer, that is responsive to communications, signals or stimuli from circuit board 4, and capable of providing electrical and/or magnetic stimulation to the tissue in which it is emplaced.

One embodiment of the invention provides two electrodes 6 arranged and configured for relatively close emplacement at an acupuncture site such that the one of electrodes 6 provides a return path for electrical and/or magnetic energy originating from the other of electrodes 6.

Electrical connector 5 may be formed integral with, hence as an extension of needle 6b, or configured to be in electrical communication therewith.

Electrical components on circuit board 4 may include a controller 14, battery 15, power switch 19, lamp 20, attenuator(s) 3 and a capacitor (not shown). Controller 14 includes a memory and other hardware elements sufficient to permit programming thereof, execute a treatment program and control necessary electrical components for administering electrical and/or magnetic stimuli via electrode 6.

Battery 15 should be sized and configured to provide sufficient energy to apparatus 10 to support its operation for a pre-determined duration, ranging from hours to days. Preferably, battery 15 is rechargeable and/or replaceable.

Power switch 19 provides for energizing apparatus 10 for effecting treatment. Preferably, power switch 19 is configured to require minimal physical force for its actuation so as to minimize dislocation or agitation of apparatus relative to the patient. Power switch 19 also should be configured to be insensitive to unanticipated contact with objects during the course of ordinary living. For example, power switch 19 may possess sensitivity to touch comparable to the screens of many portable electronic devices, such as that of an iPhone®.

Lamp 20 should be a very low-power LED or other light-emitting source for indicating that apparatus 10 is energized or operational. Lamp 20 also may emit light in a manner that corresponds with the stimuli being expressed through electrode 6, as described in greater detail below.

One or more attenuator 3 may be operatively connected with controller 14 for controlling attributes of the stimulus provided during treatment, such as intensity, duration and/or frequency.

Capacitor (not shown) provides for building up sufficient electrical charge for administering stimuli at a desired level.

Energy circuit (not shown) of circuit board 4 is operatively connected with electrical connector 5.

Backing 2, preferably, is constructed of a soft and flexible material that molds to the contours of the human body. Backing 2 should be small and unobtrusive with a relatively flat profile. Backing 2 may be skin-toned.

An embodiment of the invention provides for incorporating electrode 6, specifically anchor 6a, in backing 2. Such construction simplifies emplacement of needle 6b and adherence of backing 2, and assures accurate and reliable location and penetration of the skin through the epidermis into the dermis and/or hypodermis below.

An embodiment of the invention provides for eliminating circuit board 4 and instead embedding or mounting necessary electrical components and interconnects or circuitry onto backing 2. In combination with the foregoing embodiment, the electrical components and electrode 6 would be integral with backing 2.

Cover 7 provides for protecting apparatus 10 from contaminants and discouraging its dislodgment during treatment. Preferably, cover 7 has adhesive at least along a peripheral band 18 for adhering to skin S. Cover 7 and adhesive should be configured to provide a water tight enclosure to prevent moisture from damaging electrical components 3 or other potentially corruptible components of apparatus 10. Alternatively, the entire underside of cover 7 may include adhesive for adhering to backing 2, circuit board 4, electrical components and/or electrical connector 5.

An embodiment of apparatus 10 provides cover 7 with sufficient pliability to manipulate controls on circuit board 4, such as power switch 19 and attenuator(s) 3.

An embodiment of apparatus 10 provides cover 7 with openings (not shown) for receiving, hence revealing, and sealing around the aforementioned controls and/or lamp 20 on circuit board 4.

An embodiment of apparatus 10 provides cover 7 that is constructed of a material that is clear or sufficiently translucent to perceive light emitted from lamp 20.

An embodiment of apparatus 10 includes a reinforcement boss 21 mounted on cover, preferably centered on an axis of electrode 6. Boss 21 protects the delicate electronics on circuit board 4 and aids in accurate emplacement of apparatus 10. Preferably, boss 21 includes indicia, such as "push here," to aid a practitioner with emplacement without damaging apparatus 10.

An embodiment of apparatus 10 includes a mechanism 16 for rotating electrode 6 relative to circuit board 4. Mechanism 16 may include an electric motor (not shown) having an output shaft (not shown) terminating with a gear (not shown) that drives a second gear (not shown) mounted on electrode 6.

Figure 2:
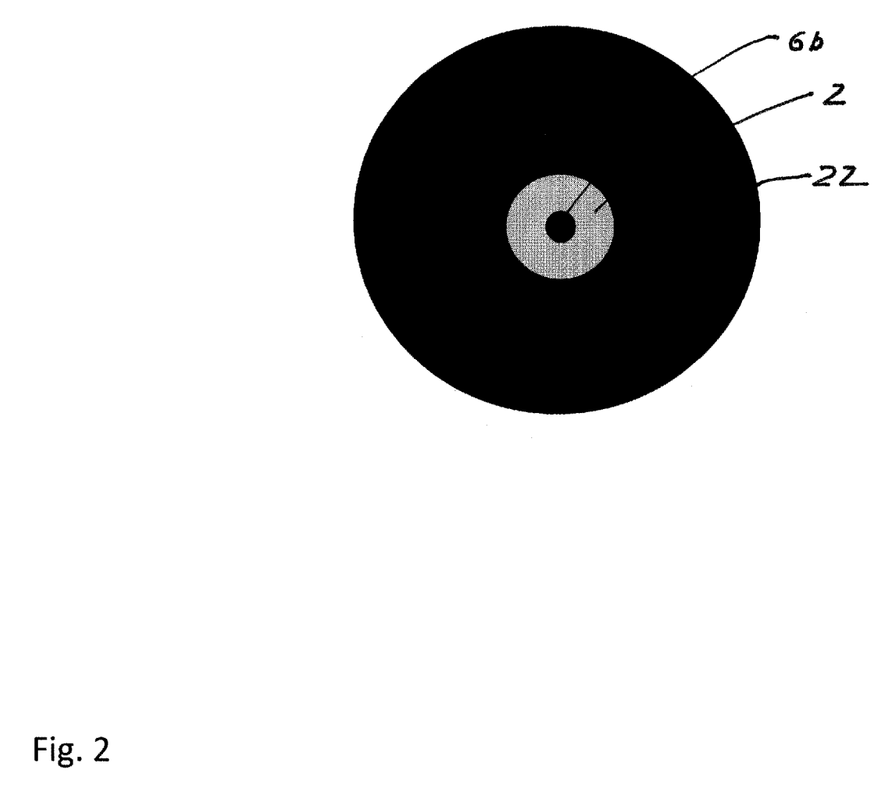
FIG. 2 is a cross-sectional detail view drawn along line II-II in FIG. 1.

Referring also to FIG. 2, an embodiment of apparatus 10 includes a surface electrode 22 operatively connected with energy circuit (not shown) circuit board 4 and disposed between circuit board 4 or backing 2, as shown, and skin S. Surface electrode 22 may be used in concert with needle 6b to stimulate localized dermal areas. Surface electrode 22 may be designed with features and geometries to enhance the localization of the delivered current, or to carefully control the path of current from a source electrode through the skin to a second return electrode.

Figure 3A:
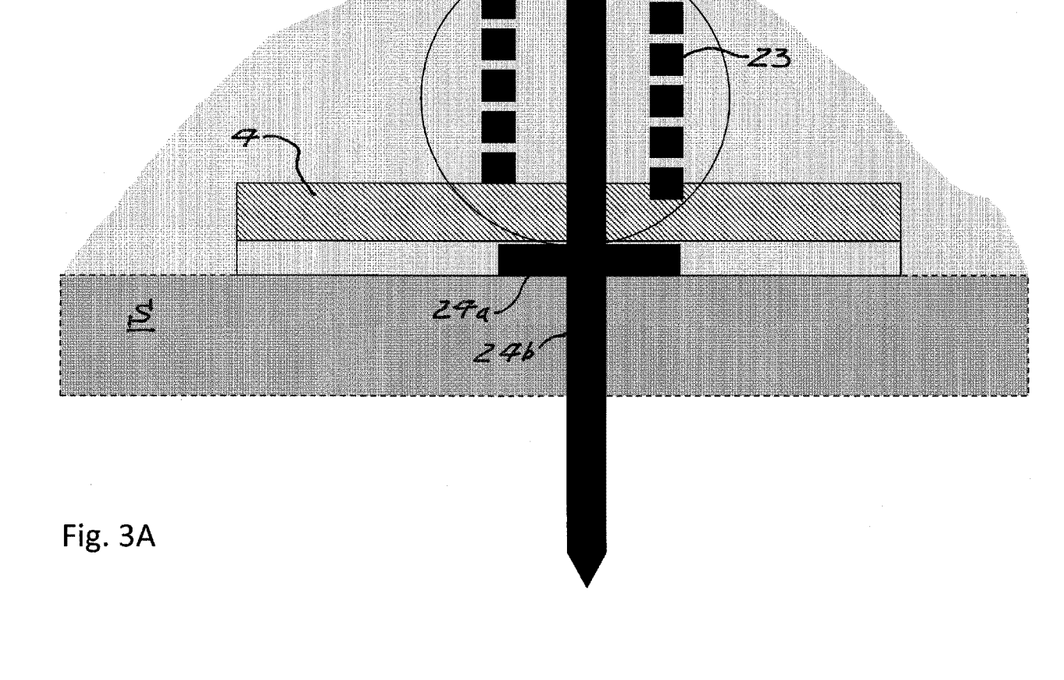
FIG. 3A is a cross-sectional detail view of another embodiment of an apparatus for neurostimulation configured according to principles of the invention.
Figure 3B:
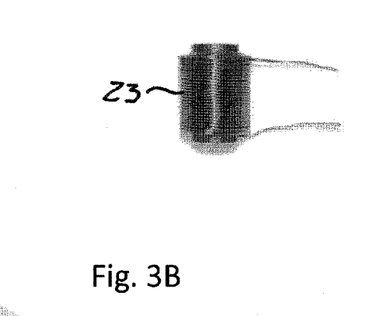
FIG. 3B is an side elevational view of section IIIB of FIG. 3A.

Referring to FIGS. 3A and 3B, an embodiment of the invention includes an electromagnetic coil 23 mounted on and operatively connected with energy circuit (not shown) of circuit board 4. Electromagnetic coil 23 is arranged and configured to conduct electrical current so as to generate a transient magnetic field in sub-dermal tissue.

An embodiment of the invention includes an electrode 24 having a needle 24b and an anchor 24a mounted relative to and operatively connected with energy circuit (not shown) of circuit board 4. Needle 24b is arranged and configured to be responsive to a transient magnetic field that electromagnetic coil 23 generates to provide a highly localized, deep magnetic field, or combination of electrical and magnetic stimulation in sub-dermal tissue.

An embodiment of the invention provides for integrating an electromagnetic coil (not shown) with needle 24b.

Figure 4A:
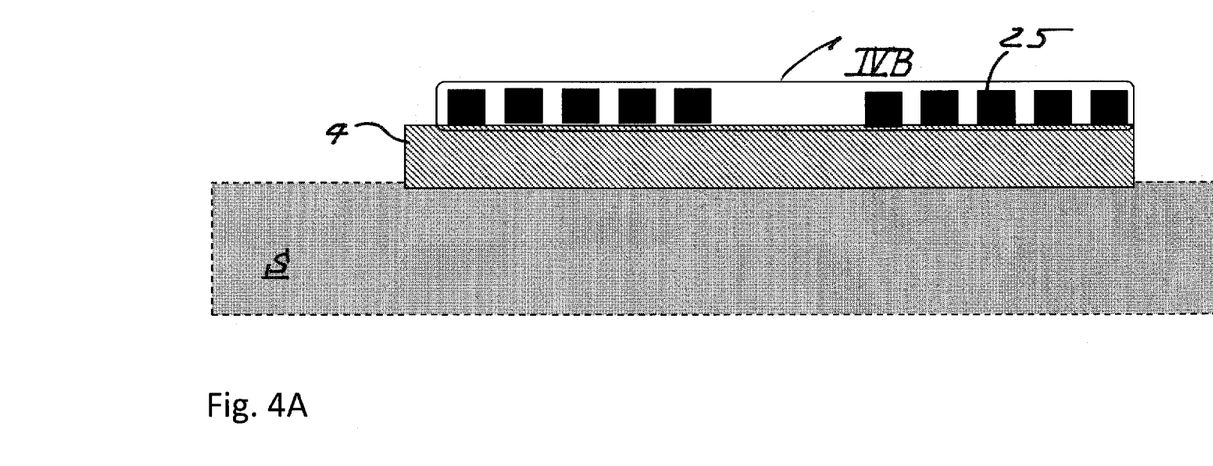
FIG. 4A is a cross-sectional detail view of another embodiment of an apparatus for neurostimulation configured according to principles of the invention.
Figure 4B:
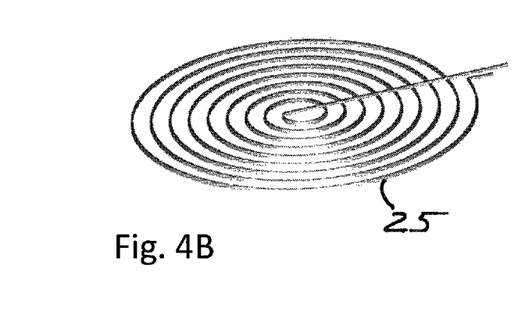
FIG. 4B is a top, front, left perspective view of section IVB of FIG. 4A.

Referring to FIGS. 4A and 4B, an embodiment of the invention includes a flat, spiral electromagnetic coil 25 mounted on and operatively connected with energy circuit (not shown) of circuit board 4. Electromagnetic coil 24 is arranged and configured to conduct electrical current so as to generate a transient magnetic field in sub-dermal tissue.

An embodiment of the invention includes an electrode (not shown) comparable to electrode 24 mounted relative to and operatively connected with energy circuit (not shown) of circuit board 4, and arranged and configured to be responsive to a transient magnetic field that electromagnetic coil 24 generates.

An embodiment of the invention provides for integrating the active elements of apparatus 10 into an article of clothing, such as a sock or a hat, for stimulating dermal tissue on the foot or head, respectively, or in another area of the body in intimate contact with the article of clothing.

Figure 5A:
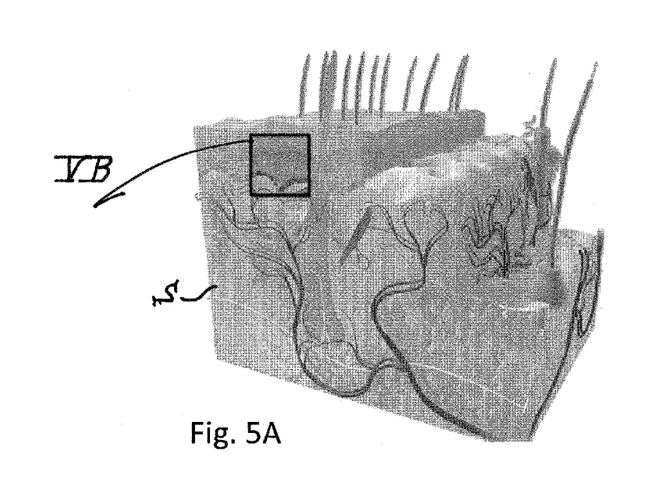
FIG. 5A is a cross-sectional detail view of human skin.
Figure 5B:
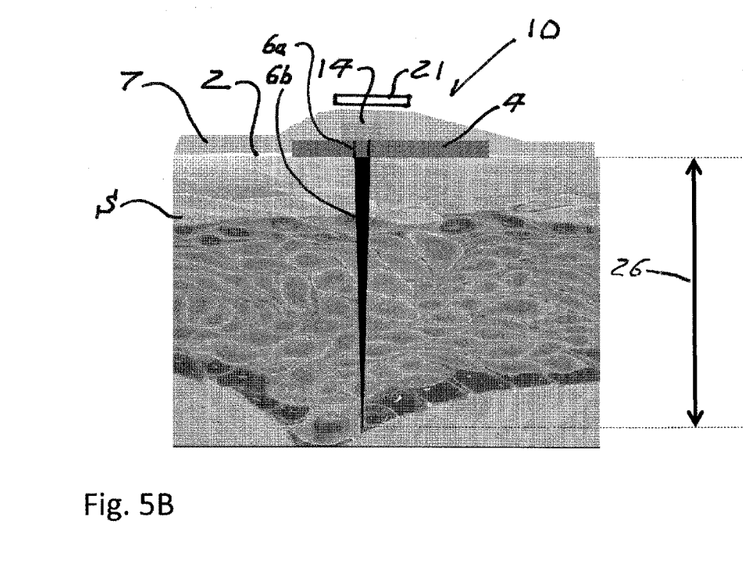
FIG. 5B is an enlarged view of section VB of FIG. 5A shown with the embodiment of FIG. 1 emplaced.

Referring again to FIG. 1 and to FIGS. 5A and 5B, in practice, an acupuncture practitioner, having located an acupuncture site on a patient, selects an appropriately-sized apparatus 10. An embodiment of the invention provides for the practitioner removing any release sheet that protect adhesive portions of backing 2 and cover 7 from premature adherence. After positioning the distal end of needle 6b proximate to the acupuncture site, the practitioner presses against boss 21, thereby urging needle 6b into skin S. Upon needle 6b attaining full emplacement, backing 2 and periphery 18 of cover 7 contact and adhere to skin S, securing needle 6b therein until it is no longer needed for treatment.

Figure 6:
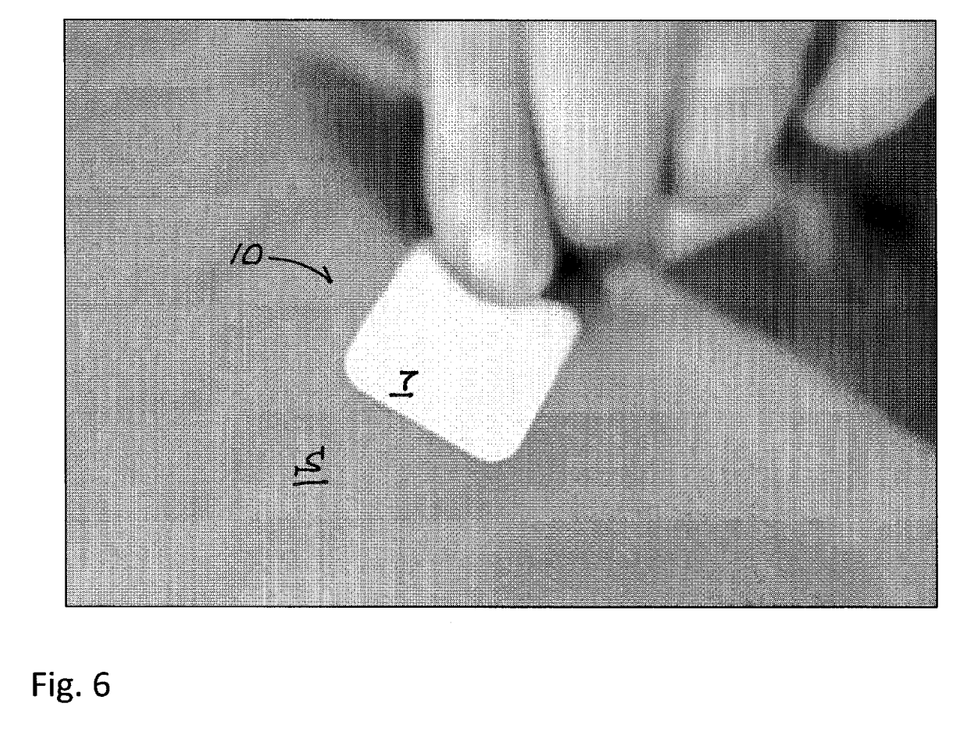
FIG. 6 is an environmental perspective view of the embodiment of FIG. 1 emplaced in skin.

Referring also to FIG. 6, once emplaced, apparatus 10 presents a low-profile, temporary fixture on skin S not unlike an ordinary bandage.

Once emplaced, if apparatus 10 employs controls, such as attenuator(s) 3, located on controller 14 or circuit board 4 for tailoring the program of stimulation desired for treatment, the practitioner would manipulate those controls accordingly.

An embodiment of the invention does not rely on controls located on apparatus 10, but rather a second controller (not shown), such as a computer or mobile device, connected to controller 14 via a hard wire interconnect (not shown) or, preferably, wireless communication, such as bluetooth, wi-fi or cellular connectivity. With such embodiments, the practitioner or patient would establish through an interface the stimulation protocols and values that would be relayed to controller 14 for subsequent execution by the electrical components. In these embodiments, apparatus 10 itself would execute the programmed instructions after its disconnection from second controller (not shown).

Once the initial programming is performed, there would be no need for further (human) intervention to allow apparatus 10 to function. However, an embodiment of the invention provides for monitoring apparatus 10 via wireless connectivity with a second controller (not shown). This would allow a practitioner or patient to monitor the current health and functioning of apparatus 10, such as battery levels.

An embodiment of the invention provides for managing multiple apparatuses 10 emplaced in a patient via a central second controller (not shown). In such embodiment, the second controller interface would allow for coordination of the stimuli expressed by the diverse apparatuses 10.

An embodiment of the invention also provides for managing and coordinating the stimuli expressed by multiple apparatuses 10, but via non-centralized, networked communications among the apparatuses 10. In other words, controllers 14 of each apparatus 10 would communicate and coordinate stimuli expressions among all of the apparatuses 10.

Figure 7:
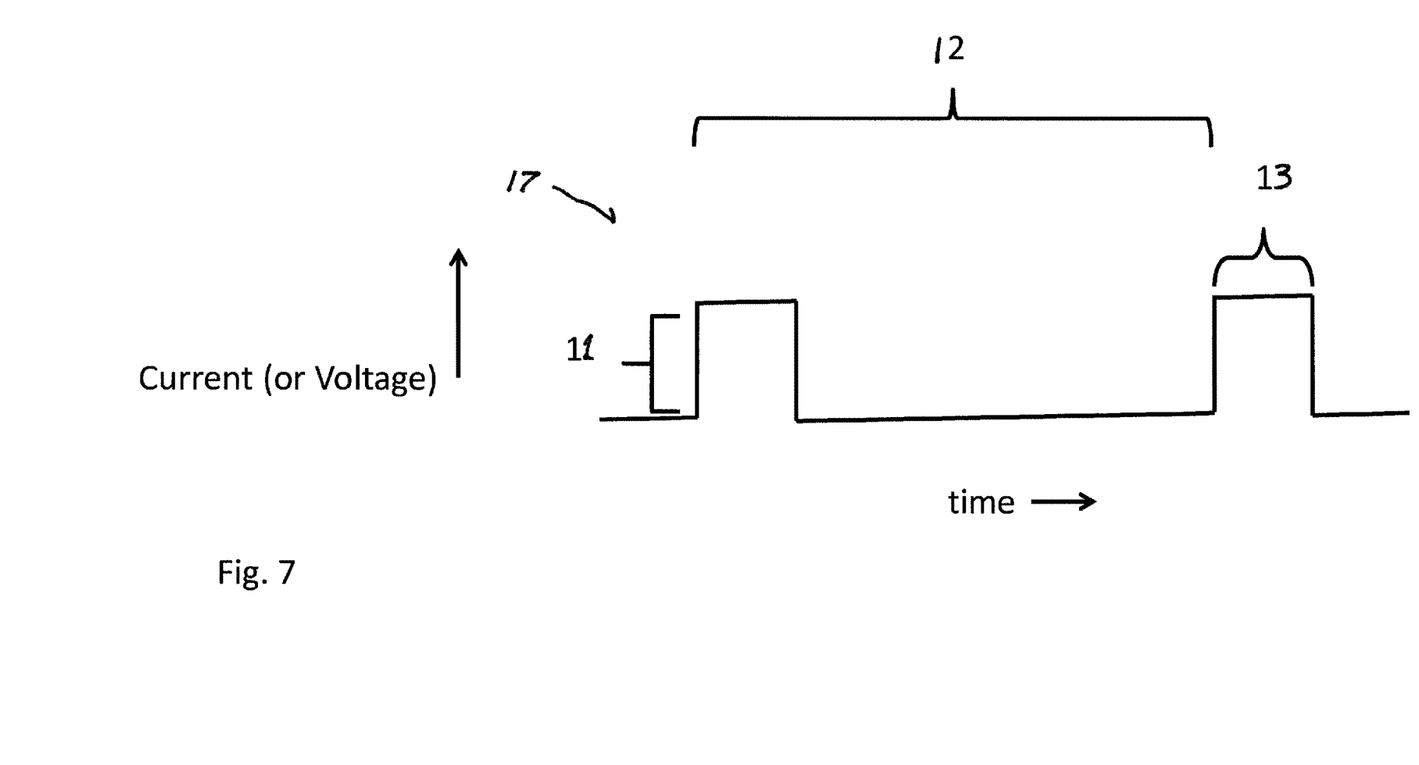
FIG. 7 is a schematic diagram of a waveform pertaining to stimulus exhibited by the invention.

Referring to FIG. 7, according to whatever treatment program is initiated, controller 14 would maintain in a register/memory thereof the out configuration of the desired output, stimuli having specified intensities 11, durations 13 and frequencies 12, defining a waveform 17. Waveform 17 may be irregular, for example, where stimuli are only desired at certain times of the day or for intensity or waveform to be varied among or between a set of stimulation parameters.

In embodiments of apparatus 10 including mechanism 16, controller 14 also is programmable to rotate electrodes 6 clockwise and/or counterclockwise at designated times.

The digital outputs of controller 14, preferably through intermediate logic gates, control the analog portion of the communications circuit (not shown), which would produce the appropriate waveform 17 defining energizing of and stimuli expressed by needle 6b. This analog portion might be a current driver or a voltage driver from a dedicated integrated circuit or a configuration of discrete components, including resistors and capacitors. Controller 14 configures the inputs of the driver or tunes aspects of the discrete components to achieve waveform 17.

Where magnetic stimulation is desired, with or without an electrode, the basic input to the coil/needle also would be a pulsed waveform 17.

The invention is not limited to the particular embodiments described and depicted herein, rather only to the following claims.

We claim:

1. Apparatus for neurostimulation comprising:
   an electrode having a distal end configured for percutaneous emplacement and a proximal end opposite thereto;
   a circuit board mounted on and in electrical communication with said electrode proximal end;

a controller mounted on said circuit board; and a mechanism on said circuit board configured to rotate said electrode proximal end relative to said circuit board;

wherein said controller is configured to cause said electrode to exhibit electronic or magnetic stimuli according to one or more parameters.

2. Apparatus of claim 1, wherein the parameters are selected from: a duty cycle, an intensity, a waveform, a frequency, and combinations thereof.

3. Apparatus of claim 1, wherein said controller is programmable.

4. Apparatus of claim 1, wherein said controller is configured to be operatively connectable with and controllable by a second controller.

5. Apparatus of claim 4, wherein said controller and said second controller are wirelessly connectable.

6. Apparatus of claim 1, further comprising adhesive configured for fixing said circuit board relative to skin.

7. Apparatus of claim 1, wherein said controller is operatively connected with said mechanism whereby said controller can cause said mechanism to rotate said electrode.

8. Apparatus of claim 1, wherein said circuit board defines a surface configured to mount on an acupuncture site, further comprising a cover configured to shield at least said circuit board and said controller from contamination and contact a peripheral area beyond said surface on the acupuncture site.

9. Apparatus of claim 1, further comprising a second electrode configured for percutaneous emplacement or contact with skin relative to said electrode so that said electrode and said second electrode define a path for electrical and/or magnetic energy.

10. System for applying neurostimulation comprising:
one or more apparatuses of claim 1; and
a second controller operatively connected with each said controller; wherein, responsive to said second controller, each said controller causes said electrode operatively connected thereto to exhibit stimuli.

11. System of claim 10, wherein said second controller is configured to control each said controller according to one or more parameters selected from: a duty cycle, an intensity, a waveform, a frequency, and combinations thereof.

12. System of claim 10, wherein said second controller coordinates said stimuli among diverse said one or more apparatuses.

13. System of claim 10, wherein said second controller is programmable.

14. System of claim 10, at least one of said one or more apparatuses each further comprising a mechanism configured to rotate said electrode relative to a circuit board mounted thereto.

15. System of claim 14, wherein said second controller is configured to cause said mechanism to rotate said electrode.

16. Method of neurostimulating comprising:
emplacing percutaneously one or more apparatuses of claim 1; and
causing one or more of the electrodes thereof to exhibit electronic or magnetic stimuli according to one or more parameters.

17. Method of claim 16, wherein the parameters are selected from: a duty cycle, an intensity, a waveform, a frequency, and combinations thereof.

18. Method of claim 16, further comprising controlling said causing with a second controller.

19. Method of claim 18, further comprising coordinating stimuli among diverse electrodes.

20. Method of claim 16, further comprising rotating one or more of the electrodes.

* * * * *